(12) United States Patent
Chan et al.

(10) Patent No.: US 7,768,639 B1
(45) Date of Patent: Aug. 3, 2010

(54) METHODS FOR DETECTING AND CORRECTING INACCURATE RESULTS IN INDUCTIVELY COUPLED PLASMA-ATOMIC EMISSION SPECTROMETRY

(75) Inventors: George C. Y. Chan, Bloomington, IN (US); Gary M. Hieftje, Bloomington, IN (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 195 days.

(21) Appl. No.: 12/212,915

(22) Filed: Sep. 18, 2008

Related U.S. Application Data

(60) Provisional application No. 60/975,360, filed on Sep. 26, 2007.

(51) Int. Cl.
*G01N 21/73* (2006.01)
(52) U.S. Cl. .......................................... 356/316; 702/85
(58) Field of Classification Search .................. 356/316
See application file for complete search history.

(56) References Cited

FOREIGN PATENT DOCUMENTS

GB 2291184 A * 1/1996

* cited by examiner

*Primary Examiner*—F. L Evans
(74) *Attorney, Agent, or Firm*—Michael J. Dobbs; Daniel D. Park

(57) ABSTRACT

A method for detecting and correcting inaccurate results in inductively coupled plasma-atomic emission spectrometry (ICP-AES). ICP-AES analysis is performed across a plurality of selected locations in the plasma on an unknown sample, collecting the light intensity at one or more selected wavelengths of one or more sought-for analytes, creating a first dataset. The first dataset is then calibrated with a calibration dataset creating a calibrated first dataset curve. If the calibrated first dataset curve has a variability along the location within the plasma for a selected wavelength, errors are present. Plasma-related errors are then corrected by diluting the unknown sample and performing the same ICP-AES analysis on the diluted unknown sample creating a calibrated second dataset curve (accounting for the dilution) for the one or more sought-for analytes. The cross-over point of the calibrated dataset curves yields the corrected value (free from plasma related errors) for each sought-for analyte.

20 Claims, 7 Drawing Sheets

METHODS FOR DETECTING AND CORRECTING INACCURATE RESULTS IN INDUCTIVELY COUPLED PLASMA-ATOMIC EMISSION SPECTROMETRY

CROSS-REFERENCE TO RELATED APPLICATIONS

This U.S. non-provisional application is related to and claims priority of U.S. provisional application 60/975,360 filed Sep. 26, 2007, which is hereby fully incorporated by reference in its entirety.

GOVERNMENT INTERESTS

The United States Government has rights in this invention pursuant to Contract No. DE-FG02-98ER14890, between the U.S. Department of Energy (DOE) and Indiana University.

FIELD OF THE INVENTION

The present invention relates to the detection and the compensation of matrix interferences and system drift in inductively coupled plasma atomic emission spectrometry.

BACKGROUND OF THE INVENTION

Inductively coupled plasma-atomic emission spectrometry (ICP-AES) is one of the most commonly used techniques for simultaneous trace multi-element analysis. However, the method is not without its shortcomings. One of the important remaining challenges is the understanding and elimination of matrix effects. Matrix effects occur when the detailed chemical composition of the sample and standard solutions are not identical; the signal strength of a particular emission line from the analyte at an identical analyte concentration changes with the concentration of other constituents (the "matrix") in the sample. As a result, analyses carried out through simple external calibration can lead to bias and analytical inaccuracy.

The behavior and mechanisms of matrix effects have been the subject of many studies. Matrix effects found in ICP-AES, according to their origins, can be divided into the three following categories: (a) spectral interferences, (b) sample introduction related, and (c) plasma related. The presence of any such interferences will typically cause error in the analysis.

Spectral interferences arise from the imperfect isolation of desired spectral lines from the composite radiation that passes the instrumental spectral window tuned to those lines. Spectral interferences, especially line overlaps, can be a significant problem in ICP-AES. Although efforts have been made to collect spectral interference data in different matrices or to build in databases in commercial ICP-AES instruments to help users select emission lines free from spectral interference in different matrices, the selection of an appropriate analytical line can still be difficult, especially for a sample with a complex or unknown matrix. Improper line selection results in a loss of detection power and analytical errors. Analytical errors caused by direct-line overlap spectral interference are difficult to recognize because the overlapping emission lines appear as one and become indistinguishable.

A currently available method to detect the presence of direct spectral-line overlap is through checking with a spectral-line database if the concentration of the matrix elements in the "unknown" sample is approximately known. These databases list all known emission lines from a particular matrix (although they may be incomplete), so an analyst can avoid employing an emission line with potential spectral-interfering wavelength positions in the analysis.

Moreover, if more than one emission line is employed for the analyte element, the emission line that suffers from spectral interference will give a significantly different (i.e., beyond experimental measurement uncertainty) analytical result than the others. However, if only two emission lines are used (in this case, results from the two emission lines are different but one cannot easily tell which one is correct), or if a few chosen emission lines suffer from spectral interferences (in this case, analytical results from different emission lines scatter and it can be difficult to determine which are the "outliers"), it may be difficult to know which emission line is free from spectral interference without referring to the wavelength database together with knowledge of the sample matrix.

For solution samples (the most common sample-introduction method for the ICP), sample-introduction-related matrix interferences are typically related to the aerosol formation or transport processes. Aerosol formation is the process of disintegration of a bulk liquid into small droplets for transport into the ICP by the carrier gas. Aerosol generation and the resultant aerosol droplet size distribution are related to the physical properties of the solution; in particular density, viscosity, and surface tension. In the presence of a matrix, these physical properties might change and result in a change in aerosol droplet size distribution. As a result, the rate of analyte injection into the plasma will be changed, and hence the sensitivity of the measurements.

For example, it has been found that acids such as sulfuric acid and phosphoric acid give rise to coarser primary aerosols because they increase the viscosity of the solutions. Although there are many possible routes by which the nebulization and transport processes can be affected by a matrix, detection of the presence of sample-introduction-related matrix effects and their subsequent correction are rather straightforward. A change of solution uptake rate, aerosol generation and transport efficiency will affect the accuracy of all elements (analytes) to the same extent, regardless of the physical properties of the elements. Thus, such interferences may be easily corrected by an arbitrary single internal standard spiked into the samples, provided that the added internal standard is chemically compatible with the sample and that the sample originally does not contain (or alternatively, contains a consistent amount of) that spiked element.

Plasma-related matrix interferences have been the focus of many studies. For plasma-related matrix interferences, the degree of interference usually depends on the characteristics of the analyte and its emission line. As a result, it is not possible to use a single internal standard for universal correction in a multi-element analysis. Consequently, a wide variety of techniques and parameters have been explored and developed to probe plasma-related matrix interferences. However, most such techniques (e.g., Rayleigh and Thomson scattering, ratios of (laser induced) atomic fluorescence to atomic emission, and computed tomography) are too complicated and instrument-demanding to be applicable to a commercial ICP-AES spectrometer intended for routine analysis.

For indicators that can be easily adaptable to a commercial instrument, the indicator should likely be based solely on the measurement of emission intensities or spectral line widths. The only effective emission-based matrix-effect indicator currently used is the ionic-to-atomic line-intensity ratio. The Mg II/Mg I ratio is commonly used to gauge the robustness of the plasma (its susceptibility to matrix interference) under different operating conditions, and even among different ICP instruments. Although very successful and applicable in many situations, the technique suffers two potential limitations. This technique requires either that the test element (e.g., Mg) can be artificially added (if not originally present in the sample), and also that it be within the linear dynamic range of the instrument (if the element is already present in the sample). Taking Mg as an example, Mg-rich samples are abundant (e.g., environmental or botanical samples) but it has been reported that the Mg II/Mg I ratio is not adequate to reflect plasma robustness for such samples because of the limited linear dynamic range of the method.

Moreover, it requires that the chosen pair of emission lines suffers no spectral interference from other constituents in the sample. Spectral interference from other constituents in the sample can be a potential problem. There is only one strongly emitting Mg I line and if any other spectral line overlaps with it, the calculated Mg II/Mg I ratio is erroneous. Although an ionic and neutral-atomic line pair from a more line-rich element might be substituted for Mg, most elements exhibit only weak neutral-atomic emission lines in the ICP. Moreover, emission from each spectral line is generally weaker for a line-rich element, so a higher concentration of the test element is required to avoid spectral interference from other constituents of the sample.

Once the presence of a plasma-related matrix interference is noted, conventional methods exist to cope with such issues. Four conventional techniques have been used: matrix separation; matrix matching between the sample and the standards; by the use of internal standards; and by standard additions. While these techniques can solve the problem of matrix interference when correctly applied, there are shortcomings.

For example, matrix separations are typically laborious and can lead to analyte loss. Also, the identity of the interfering matrix needs to be known before an efficient separation method can be applied. Matrix-matching requires knowledge of the approximate concentrations of the major sample constituents and therefore, may require an additional pre-analysis. Internal standardization requires a prior-analysis study to find the correct internal standard(s) that change similarly with the analyte and, in general, more than one internal standard is usually required in a multi-element analysis. Standard addition requires spiking ("addition") of the analyte into the sample and several additions are usually required for a single sample, which considerably lengthens the total analysis time. Moreover, it has been shown through statistical analysis that the concentration ratios of the spiked sample and the original sample have a critical impact on the precision of the x-intercept of the standard-addition curve through extrapolation (i.e., the final analysis result).

It has been shown that the concentration of the analyte in the spiked sample should preferably be at least two times the original concentration and that precision degrades in an exponential fashion when the spiked concentrations are lower than the original concentration. Also, the concentrations of the spiked analyte should not be too high as the principle of standard addition assumes that the matrix is invariant and that there are identical matrix effects in both the original and the standard-spiked samples. This assumption can be met only if the added standard is not too large compared to the original concentration of the analyte (i.e., roughly within one order of magnitude). This problem is particularly acute considering that ICP-AES is a simultaneous multi-element analysis technique, which means that multi-element spikes must be added concurrently.

Therefore, the margin is comparatively narrow for the concentration of the spike to be added and the absolute amount is clearly sample-dependent. In other words, to yield results with reliable precision and accuracy, the concentration of the analyte in the sample should be known semi-quantitatively. To summarize, all four of these conventional techniques require either a separate study or some prior knowledge about the unknown sample, which requires an additional pre-analysis to obtain such information. Currently, there is no on-the-fly method available to compensate for plasma-related matrix interference for a completely unknown sample. In addition, all of the above-mentioned techniques require the addition of foreign reagents to the sample and, therefore, are more prone to human error and chemical impurities.

Another major source of analytical errors in ICP-AES is instrumental drift. The result of such drift is the need for frequent recalibration, which is time-consuming. It is common in routine analysis to run regularly a so-called quality-control (QC) sample of predefined concentration in order to monitor system drift, and to serve as a decision tool as to whether recalibration is required. If drift is found between two calibrations, there is no general rule to correct the intervening data to compensate for the drift; although it is often assumed that drift is linear with time, that assumption is not always valid. Although running QC samples is effective for monitoring system stability, it can be difficult to determine how often a QC sample must be run. Preferably, instrumental drift correction is performed in an on-line fashion together with the analysis of an unknown sample. With this approach, immediate corrective action can be taken once a drift is noted.

SUMMARY OF THE INVENTION

A method for detecting and possibly correcting inaccurate results in inductively coupled plasma-atomic emission spectrometry (ICP-AES). ICP-AES analysis is performed across a plurality of selected locations in the plasma on one or more known samples each comprising one or more sought-for analytes, collecting the light intensity at one or more selected wavelengths (emission lines) emitted by the one or more sought-for analytes, to create a calibration dataset. ICP-AES analysis is preferably performed on a plurality of known samples having a variety of concentrations for each sought-for species. ICP-AES analysis is performed across the plurality of selected locations in the plasma on an unknown sample, collecting the light intensity at the one or more selected wavelengths corresponding to emission lines of the one or more sought-for analytes, creating a first dataset.

The first dataset is then calibrated with the calibration dataset creating a calibrated first dataset curve. If the calibrated first dataset has a variability along the plurality of selected locations within said plasma for a selected wavelength, errors are present.

Once errors are detected, plasma related errors can be corrected by diluting the unknown sample and performing additional ICP-AES analysis. ICP-AES analysis is performed on the diluted unknown sample across the plurality of selected locations in the plasma, collecting the light intensity at the one or more selected wavelengths, wavelengths corresponding to emission lines of the one or more sought-for analytes, creating a second dataset.

The second dataset (from the diluted unknown sample) is then calibrated (while also accounting for the dilution) with the calibration dataset creating a calibrated second dataset curve. The cross-over point of the calibrated first dataset curve and the calibrated second dataset curve for each selected wavelength yields a corrected analytical result, a result free from plasma related errors.

In one illustrative embodiment, the method may provide an indicator that simultaneously flags inaccuracies in analytical results due to the presence of interferences caused by any one of the three major matrix-effect categories (i.e., spectral interference, sample introduction-related, and plasma-related matrix interferences) and also instrumental drift in ICP-AES, in an online fashion during an analysis so immediate remedial work can be undertaken once an interference/drift is flagged. This illustrative method also requires no additional external chemical agent.

Using an indicator for flagging spectral interference in a multi-line analysis, this illustrative method may automatically determine which light intensity at one or more selected wavelengths suffer from spectral interference (even in the case of direct spectral-line overlap) without referring to any spectral-line database and with no prior knowledge about the matrix of the unknown sample. The illustrative indicator does not require the addition of any external reagents into the sample. In contrast to the ionic-to-atomic line-intensity ratio method for flagging plasma-related matrix interferences, the illustrative indicator does not require a test element and is specific for the sought-for elements and spectral lines to be used.

In one illustrative method the indicator can determine the existence of system drift in an online fashion during the analysis of the unknown sample. In the illustrative method, for plasma-related matrix interference compensation and unlike other currently known methodologies, the method does not require any prior knowledge about the content of the unknown sample nor the addition of external reagents, or additional sample handling steps, excepting simple dilution. The illustrative method for plasma-related matrix interference compensation can be used on-the-fly during an analysis, even when the identity of the matrix is unknown. The illustrative method also can be easily automated.

DETAILED DESCRIPTION OF THE INVENTION

Figure 1B:
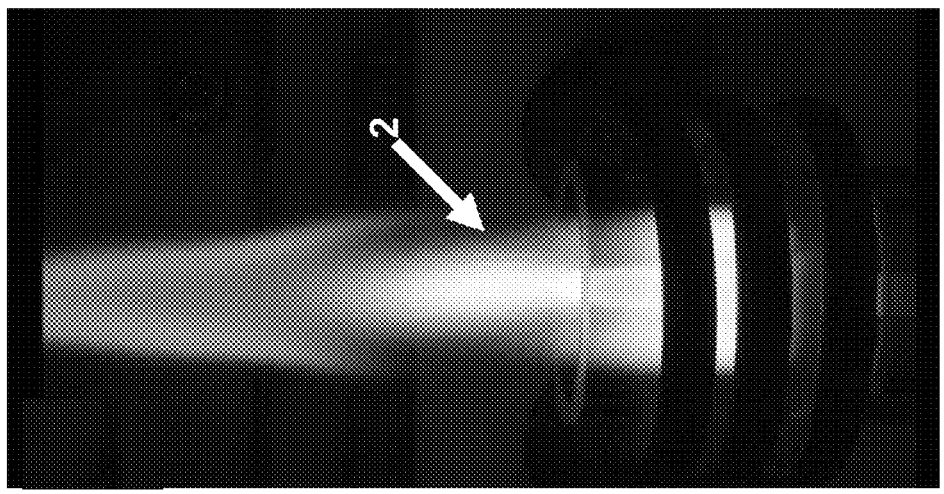
FIG. 1b depicts the typical geometry of an inductively coupled plasma (ICP) torch into which is aspirated a high concentration of yttrium solution.

A method for detecting and possibly correcting inaccurate results in inductively coupled plasma-atomic emission spectrometry (ICP-AES). ICP-AES analysis is performed across a plurality of selected locations in the plasma on one or more known samples each comprising one or more sought-for analytes, collecting the light intensity at one or more selected wavelengths (emission lines) emitted by the one or more sought-for analytes, to create a calibration dataset. ICP-AES analysis is preferably performed on a plurality of known samples having a variety of concentrations for each sought-for species. ICP-AES analysis is performed across the plurality of selected locations in the plasma on an unknown sample, collecting the light intensity at the one or more selected wavelengths corresponding to emission lines of the one or more sought-for analytes, creating a first dataset.

The first dataset is then calibrated with the calibration dataset creating a calibrated first dataset curve. If the calibrated first dataset has a variability along the plurality of selected locations within said plasma for a selected wavelength, errors are present.

Once errors are detected, plasma related errors can be corrected by diluting the unknown sample and performing additional ICP-AES analysis. ICP-AES analysis is performed on the diluted unknown sample across the plurality of selected locations in the plasma, collecting the light intensity at the one or more selected wavelengths corresponding to emission lines of the one or more sought-for analytes, creating a second dataset.

The second dataset (from the diluted unknown sample) is then calibrated (while also accounting for the dilution) with the calibration dataset creating a calibrated second dataset curve. The cross-over point of the calibrated first dataset curve and the calibrated second dataset curve yields a corrected analytical result, a result free from plasma related errors.

Preferably, the one or more selected wavelengths of light are selected to include all possible wavelengths (element lines), generated during ICP-AES. The one or more selected wavelengths are more preferably wavelengths of light emitted by the one or more sought-for analytes. In a preferred embodiment, the one or more selected wavelengths are wavelengths key in identifying the one or more sought-for analytes.

Preferably, the sought-for analyte is one or more chemical elements, substances, etc. which the user desires to detect or more preferably quantify, during ICP-AES analysis. Preferably a variety of concentrations of each sought-for analyte is analyzed to increase the accuracy of detection.

Preferably, the plurality of locations within the plasma are located along the height, width or a combination thereof of the plasma. In a preferred embodiment, the plurality of locations within the plasma are located along the height of the plasma. Preferably, the plurality of locations within the plasma are located along the height of the plasma at a height above the load coil (HALC) between and including about 0 and 20 mm.

The cross-over point is the point at which the analytical results of the calibrated first dataset curve equals those of the calibrated second dataset curve (accounting for dilution) for a given wavelength and location within the plasma. This analytical result is a corrected analytical result having no plasma related errors.

In one embodiment, locations within the plasma are located along the width of the plasma. This embodiment may be preferable depending on the cause of the ICP-AES errors and on the design of a particular instrument, as well as on the sample.

In yet another alternative embodiment, locations within the plasma are located along both the width and height of the plasma. This embodiment may be preferable depending on the cause of the ICP-AES errors and on the design of a particular instrument, as well as on the known sample and unknown sample.

Calibrated First Dataset Curve and Calibrated Second Dataset Curve

Preferably, the calibrated first dataset curve and the calibrated second dataset curve are each produced using one or more mathematical equations, (termed calibration equations) or their graphical equivalents, derived from the calibration dataset correlating the light intensity at the one or more selected wavelengths to the true concentration of each sought-for analyte.

For example, for a given ICP-AES plasma, calibration dataset curves for a plurality of locations within the plasma are determined by performing ICP-AES analysis on known samples containing known concentrations of Mg in an aqueous matrix. Preferably, more than one known sample is used to construct the calibration dataset with varying concentrations of Mg for the accurate determination of analyte concentration. As the amount of Mg in each solution is known, the calibration dataset curve at each selected location in the plasma is designed whereby the light intensity detected at the wavelength emitted by Mg multiplied by the calibration equations derived from the calibration dataset yields the actual concentration of Mg for the known sample.

Therefore in this embodiment, the calibrated first dataset curve comprises apparent concentrations for each sought-for analyte. Likewise, the calibrated second dataset curve comprises apparent concentrations for each sought-for analyte. In the absence of errors, both curves would be exactly the same. Therefore, if the curves are not the same and there are errors, the cross-over point is the point at which there is no error and the point yielding the true sought-for analyte concentration. Contrarily, points outside of the cross-over point yield results having errors.

In the alternative, the calibrated first dataset curve and the calibrated second dataset curve are each produced using one or more mathematical equations, (termed calibration equations) or their graphical equivalents, derived from the calibration dataset correlating the light intensity to some normalizing value (e.g. relative intensity and normalized emission profiles). This embodiment may be beneficial in situations where normalized or relative values are sufficient and actual concentrations of a sought-for analyte are unnecessary.

The light intensity at one or more selected wavelengths emitted by the sought-for species will be affected by dilution of the unknown sample. However, the dilution of the unknown sample will linearly affect the light intensity at one or more selected wavelengths emitted by the sought-for species within reasonable bounds, preferably by a dilution factor of 20 or less, more preferably of 10 or less. In a preferred embodiment, the unknown sample is diluted by a factor of 2. Therefore the observed light intensity is adjusted for dilution by multiplying by the dilution factor. For example, the detected light intensity for a sample diluted by a factor of two will be multiplied by the corresponding dilution factor (two), as well as multiplied by the calibration equations derived from the calibration dataset.

As the light intensity at a selected wavelength will naturally vary along different locations within plasma due to various factors (e.g. ICP torch design, ICP torch defects, gas flow, optics, etc.), the calibration dataset must be taken to account for the variability across the plasma. Further samples, such as the first dataset from the unknown sample, will follow along the same curve or shape of the calibration dataset in the absence of any errors. However, if errors (e.g. spectral interferences, sample introduction related, plasma related errors, or drift) are present in a dataset, the dataset will have a curve shape different from the calibration dataset curve, indicating the presence of errors.

Figure 1A:
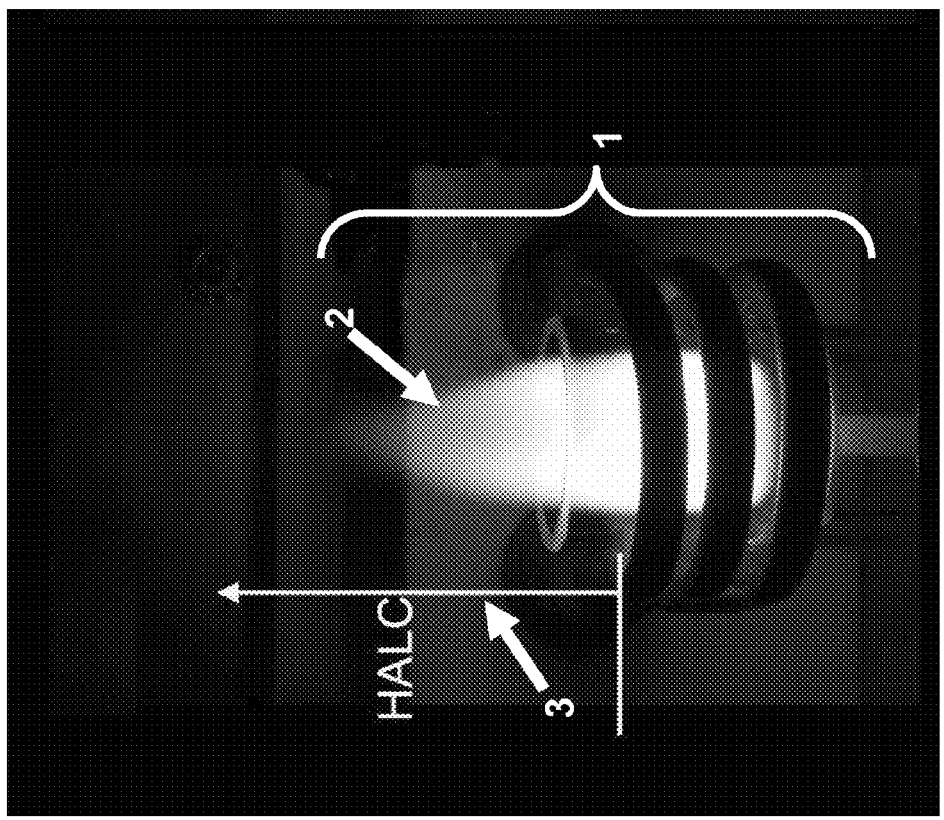
FIG. 1a depicts the typical geometry of an inductively coupled plasma (ICP) torch.

FIG. 1a and FIG. 1b

FIG. 1a and FIG. 1b depict the typical geometry of an Inductively coupled plasma-atomic emission spectrometry ICP torch and plasma 1. Vertical distance in the plasma 2 is often referred to in terms of height above the load coil (HALC) 3. One illustrative embodiment method employs a measurement of the vertically resolved atomic emission distribution of an analyte within the ICP to detect and compensate for matrix interferences in ICP-AES.

FIG. 2

Figure 2:
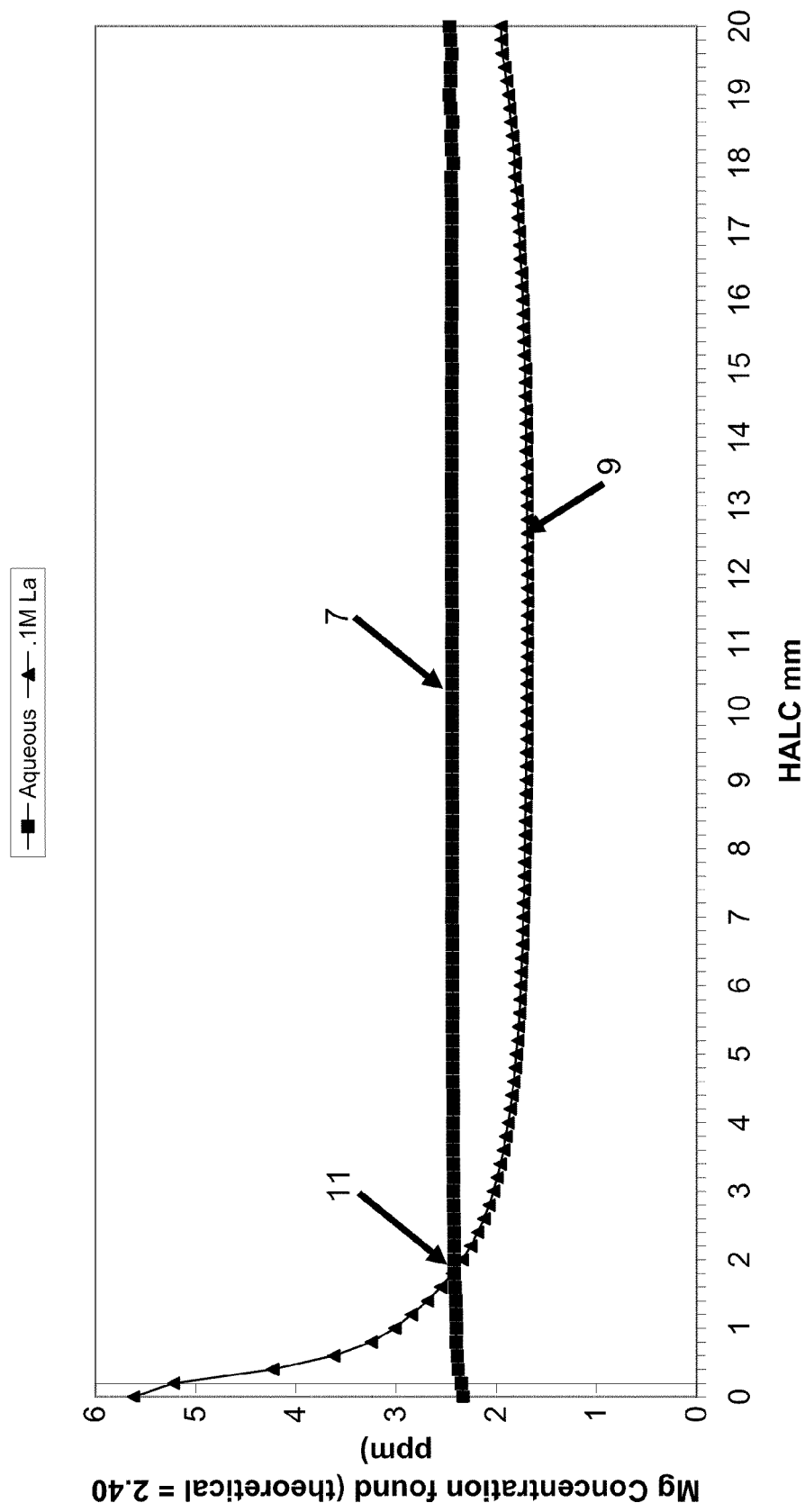
FIG. 2 depicts a graph of the apparent concentration (calibrated datasets) from a sample having a matrix effect and a sample not having a matrix effect.

The matrix effect illustratively shown in FIG. 2 belongs to the plasma-related type. Analysis of a 2.4 ppm Mg aqueous solution 7 (black squares) yields apparent concentration values that are the same along the vertical profile of the plasma. However, when 2.4 ppm Mg is analyzed in a solution also containing 0.1 M La 9, a matrix effect occurs.

The matrix effect influences analyte emission across the plasma, resulting in apparent concentration values that differ as a function of HALC position within the plasma. This dependence signals a matrix effect. When the vertical atomic emission profile of an element in a known sample (i.e. without a matrix effect) is compared to that observed for the same element when a matrix effect is occurring, large differences can be seen. In one typical matrix-effect situation, the analyte emission is enhanced at points lower in the plasma and depressed at higher HALC locations when a matrix effect occurs. While each matrix effect mechanism might cause different types of enhancement or depression, each changes the vertical emission profile of an element from that observed when the same element is analyzed in the absence of matrix effects.

In the illustrative example of plasma-related matrix interference shown in FIG. 2, the matrix effects change from an enhancement at very low positions in the plasma to a depression at higher positions. The transition where the enhancement is balanced by the depression results in a spatial region with no apparent matrix effects, or the "cross-over point 11." Obviously the exact location of the matrix-effect cross-over point is very attractive in practical analysis because there is no observed matrix effect (i.e., accurate analytical results can be obtained) at that particular plasma observation location. However, its utilization is not straightforward because this location depends both on the analyte wavelength of light and on the matrix composition (i.e., it might vary across different samples). One illustrative method for compensation of plasma-related matrix interference is based on an approach for in-situ determination of the location of this cross-over point 11.

FIG. 3 and FIG. 4

Figure 3:
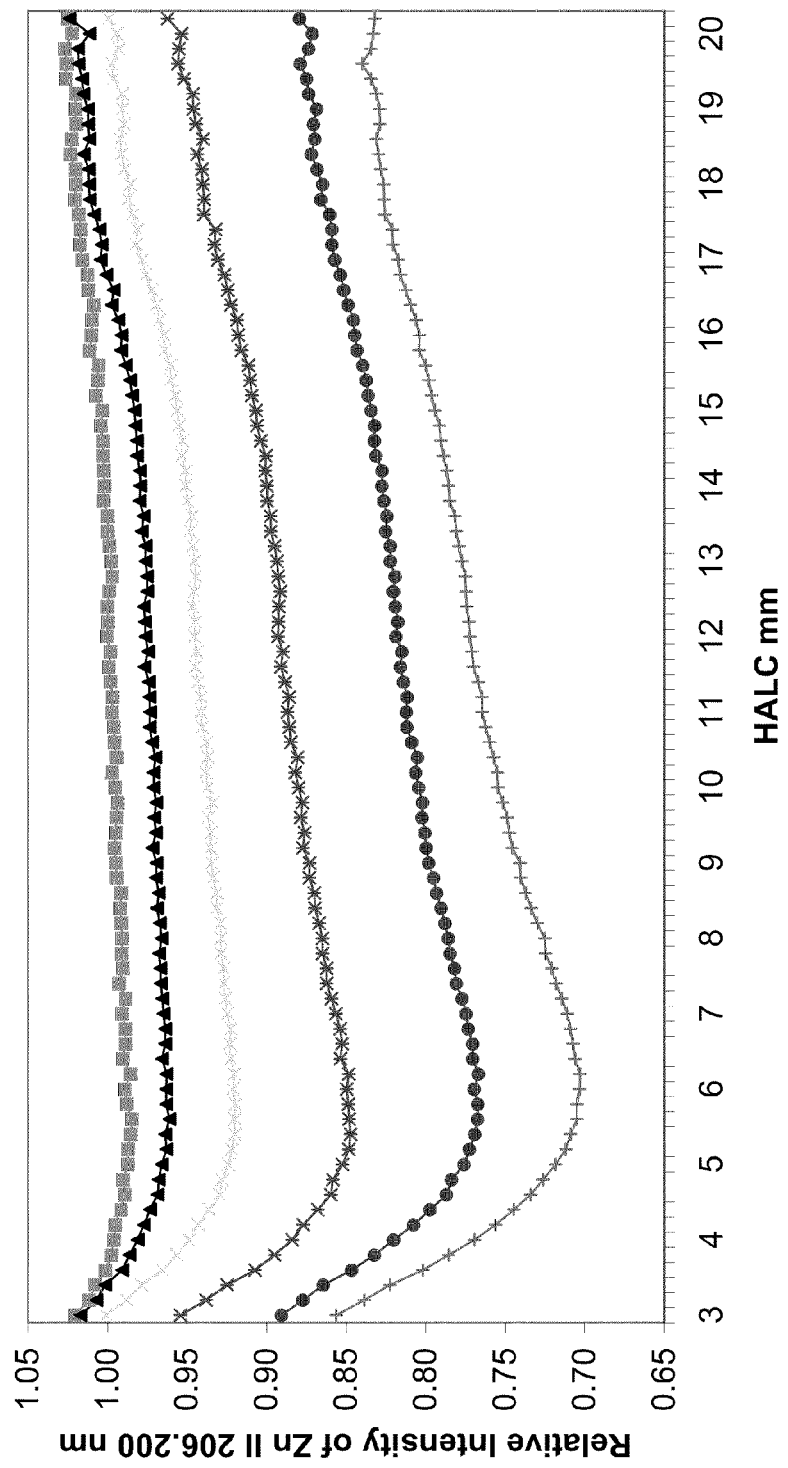
FIG. 3 depicts the relative-intensity of light profile of a representative emission line Zn II 206.2 nm under the influence of various concentrations of nitric acid ($HNO_3$).
Figure 4:
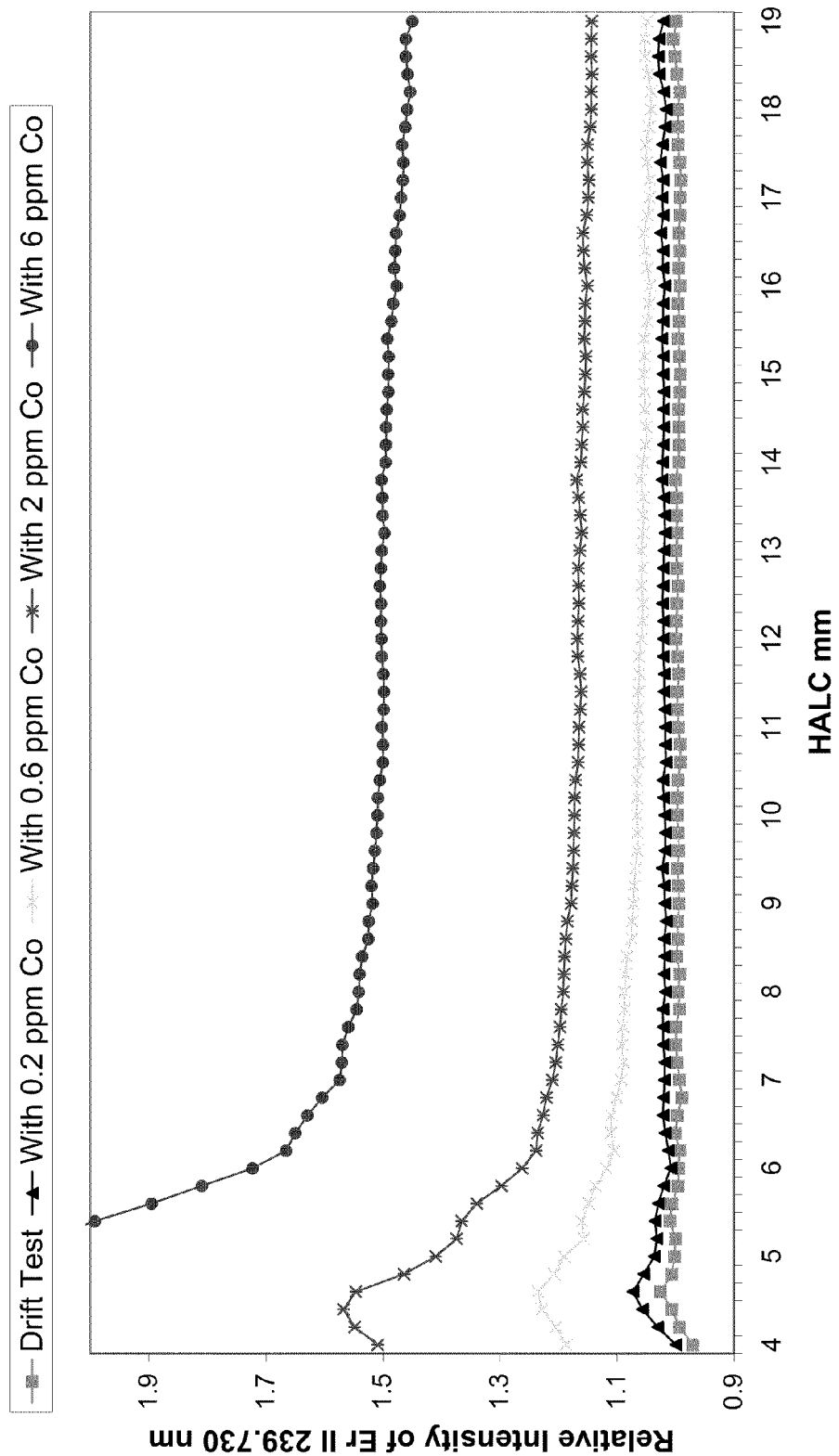
FIG. 4 depicts the relative-intensity of light profile of the Er II 239.730 nm spectral line under the influence of co-existing Co from 0.2 ppm to 6 ppm.

FIG. 3 and FIG. 4 show illustrative examples of the curvature in the vertical relative-intensity of light profile induced by sample-introduction-related interference and spectral interference, respectively. The relative-intensity of light is the intensity of light detected (in the presence of errors) divided by the intensity of light of the sample in the absence of errors. FIG. 3 depicts the relative-intensity of light profile of a representative emission line of Zn II at a wavelength of 206.2 nm under the influence of various concentrations of nitric acid (HNO$_3$). FIG. 4 depicts the relative-intensity of light profile for Er II emission at 239.730 nm under the influence of co-existing Co from 0.2 ppm to 6 ppm.

FIG. 5

Figure 5:
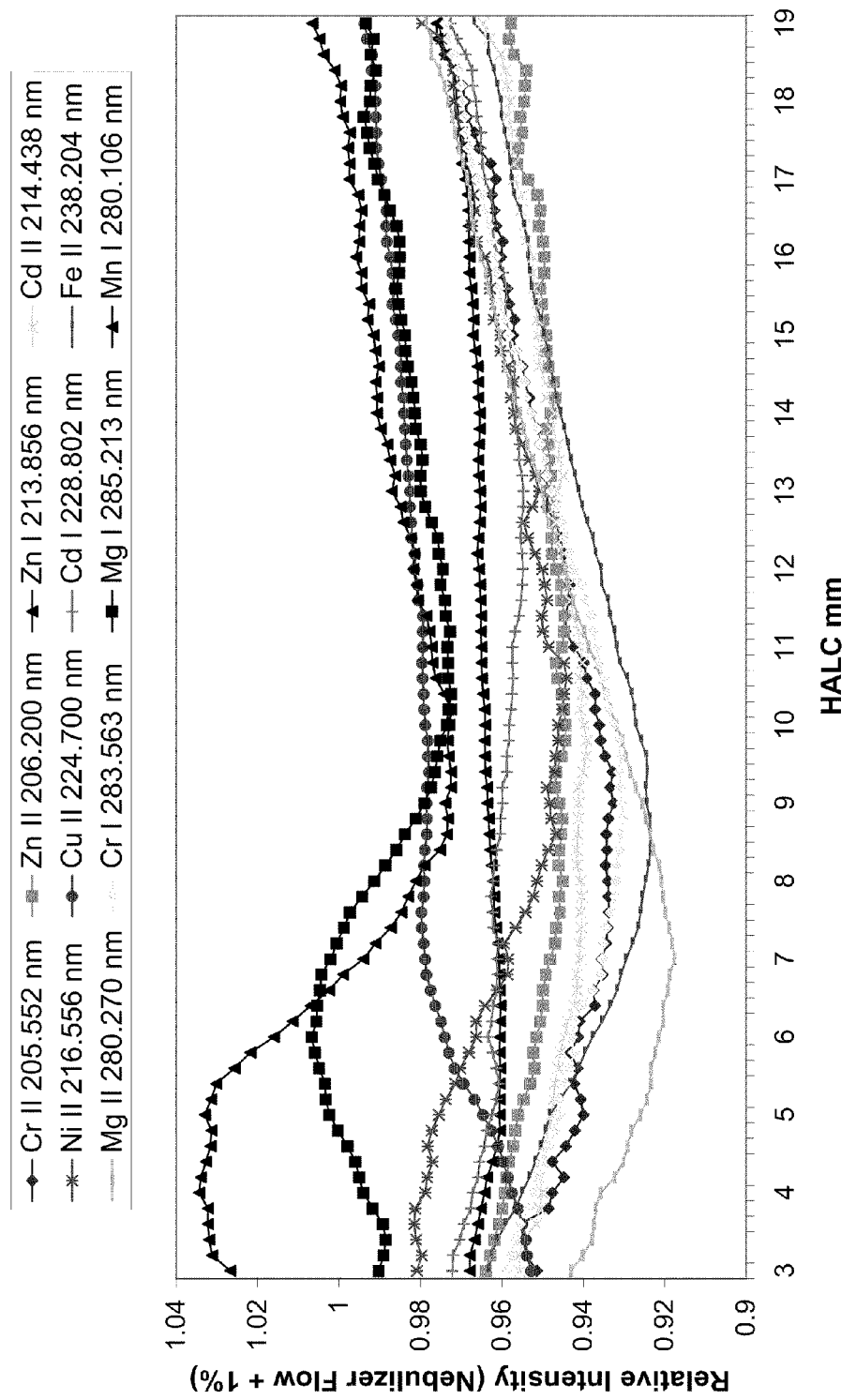
FIG. 5. depicts the influence of nebulizer gas flow rate increase by an amount of 1% to mimic instrumental drift, on the vertical relative-intensity of light profiles of a pool of emission lines.

Instrumental drift also induces curvature in the vertical relative-intensity of light profile, as demonstrated by an artificially induced drift in the central channel gas flow rate, as presented in FIG. 5. Vertically resolved analyte emission may be an effective and efficient alarm indicator for several types of matrix effects and sources of system drift.

FIG. 6

Figure 6:
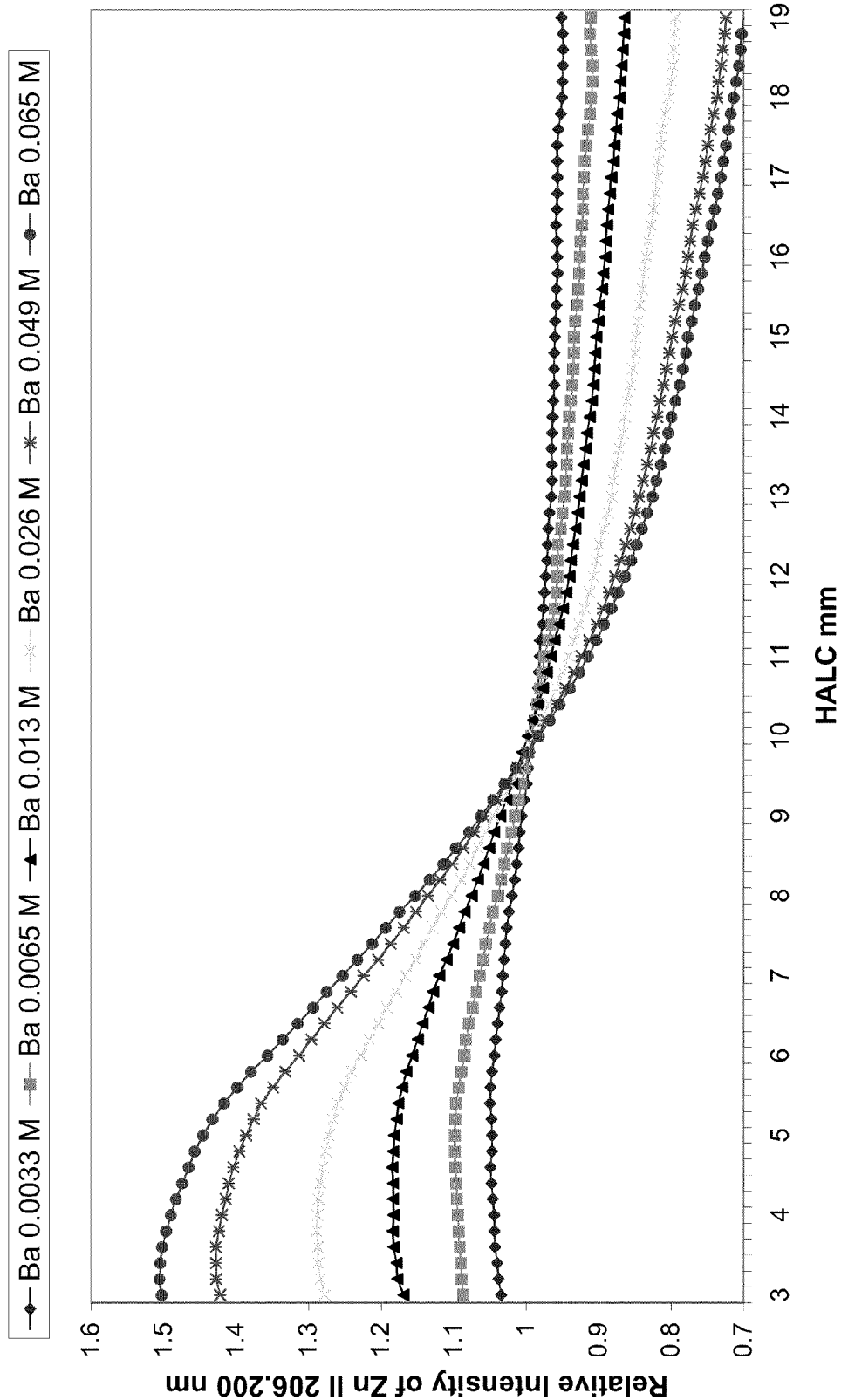
FIG. 6 depicts vertical relative-intensity of light profiles of a representative emission line Zn II 206.200 nm line under the influence of various concentrations of Ba matrix.

For plasma-related matrix effects, the location of the cross-over point is practically invariant for a particular analyte wavelength of light when the concentration of the matrix is varied (see FIG. 6). As a result, it is possible to determine in-situ the location of the cross-over point for substantially all analyte wavelengths of light (emission lines) in a sample by means of a one-step sample dilution.

The procedure for this illustrative matrix-effect compensation is as follows: A sample is first analyzed using the whole plasma vertical profile with spatial resolution, as previously described. Preferably, a calibration dataset is determined along the height of the plasma at a height above the load coil (HALC) between and including about 0 and 20 mm. If a plasma-related matrix effect is found (from curvature in the apparent concentration curve such as FIG. 2), the original sample is diluted preferably by a factor less than 20, more preferably by a factor less than 10. In a preferred embodiment, the original sample is diluted by a factor of two. The diluted sample is analyzed again. Because the matrix concentration in this diluted sample is reduced, the associated matrix effect is also lessened (i.e., the signal enhancement low in the plasma becomes less enhanced while the signal depression high in the plasma becomes less depressed).

The extent of the matrix effect is identical between the original sample and the diluted sample at one and only one location—the cross-over point. In fact, the extent of the matrix effect is zero (i.e., there is no observed matrix effect) at this point. Of course, the sought-for analyte concentration, and therefore, its emitted light intensity, is also reduced by the dilution but this effect can be easily compensated simply by multiplying the light intensity of the second dataset (diluted unknown sample) by the dilution factor. This is possible because ICP-AES is known to have a very wide linear dynamic range (the relationship between concentration and emission signal). Since the location of the cross-over point does not shift with matrix concentration, the intersection of the apparent concentration profiles of the original and diluted samples (with dilution factor corrected) can correctly locate the cross-over point and give the accurate analyte concentration in the sample.

This illustrative method was verified with various single-element matrices (0.05M Na, Ca, Ba and La) and mixed-element matrices (mixture of Na—Ca, Ca—Ba, plant sample digest).

Figure 7:
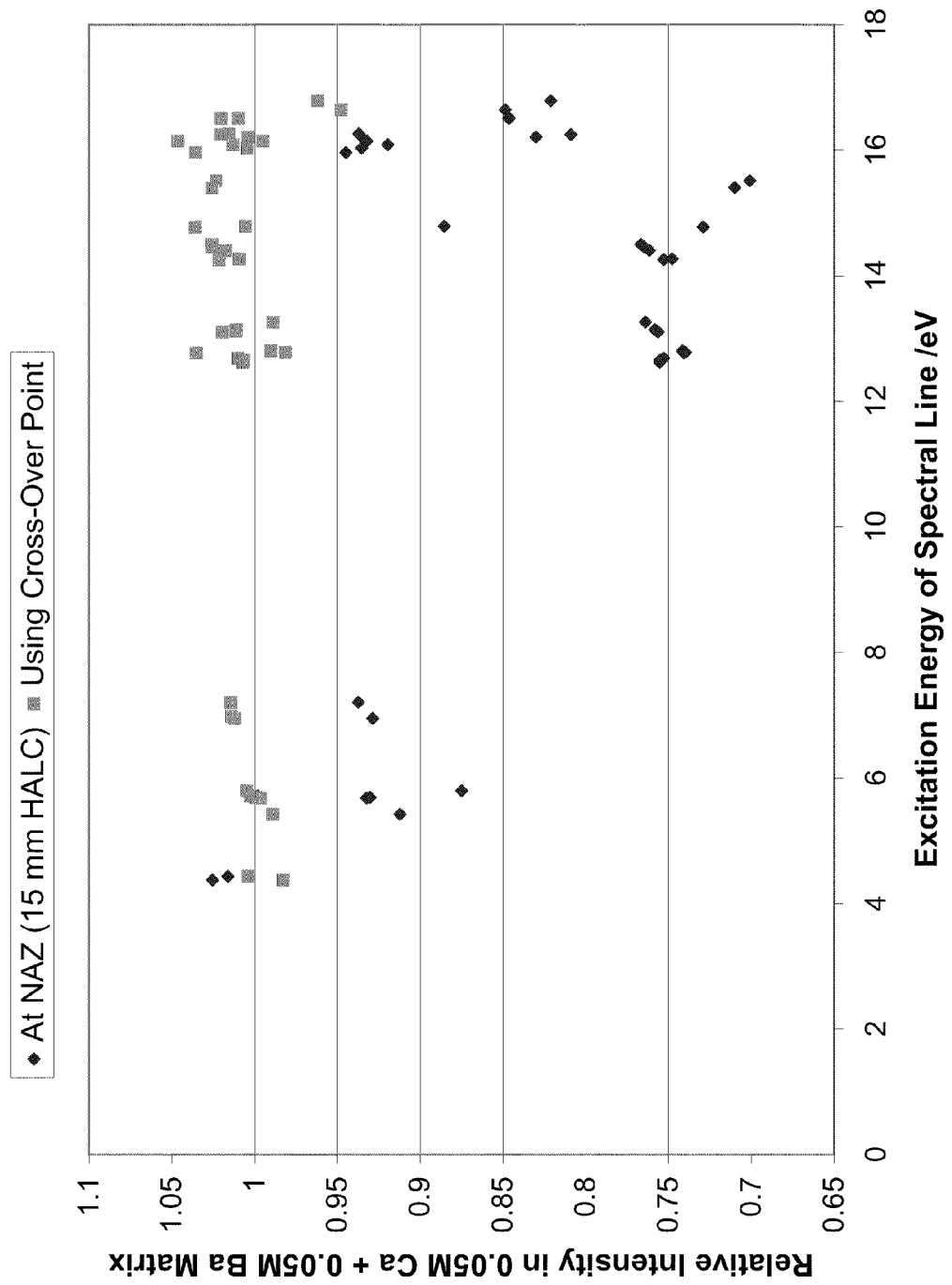
FIG. 7 depicts a comparison of analytical accuracy in a multi-element analysis obtained in the normal analytical zone NAZ of the plasma at 15 mm height above the load coil (HALC) vs. results obtained at in-situ determined cross-over point for individual emission lines.

In certain environments, the inaccuracy in emission intensity or concentration due to the matrix effect could be as large as about 30% for conventional measurements in the normal analytical zone but is improved to within 5% using the above described method (see FIG. 7).

In summary, the illustrative methods described above may provide a simple and efficient warning signal for flagging any interferences or instrumental drift during a chemical (elemental) analysis with inductively coupled plasma-atomic emission spectrometry (ICP-AES). The presence of interferences or instrumental drift, without the awareness of an operator and subsequent correction, will lead to an analytical error. A warning signal may draw attention so that immediate remedial work can be undertaken.

Furthermore, all three major categories of interferences found in ICP-AES (those in the plasma, those in the sample-introduction system and those caused by spectral overlap), as well as instrumental drift, can be detected using the methods described above at the same time. The methods described above are applicable to a wide range of sample types in an on-line fashion during analysis. The methods described above, unlike other available methods, require no addition of external reagents to the sample nor any prior knowledge about the content of the unknown sample. The methods described above are readily adoptable on commercial ICP-AES spectrometers.

The methods described above for matrix interference compensation, unlike other currently known methodologies, do not require any prior knowledge about the content of the unknown sample. The methods described above for matrix interference compensation do not require additional sample preparation except simple dilution and can be used for the correction of plasma-related matrix effects caused by a wide range of matrices. Both the indicator and the proposed method for plasma-related matrix interference compensation can be easily automated and require no extra input or additional sample treatment from the analyst.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provisions of 35 U.S.C. §112, ¶6.

The invention claimed is:

1. A method for improved inductively coupled plasma-atomic emission spectrometry (ICP-AES) comprising:
    performing ICP-AES analysis on one or more known samples using an inductively coupled plasma, obtaining a calibration dataset comprising the light intensity at one or more selected wavelengths for a plurality of selected locations within said plasma;
    each said known sample comprising one or more sought-for analytes;
    said step of performing ICP-AES analysis on one or more known samples comprising performing ICP-AES analysis on a plurality of concentrations of each said sought-for analyte;
    said one or more selected wavelengths emitted by said one or more sought-for analytes;
    performing ICP-AES analysis on an unknown sample using said inductively coupled plasma, obtaining a first dataset comprising the light intensity at said one or more selected wavelengths for said plurality of selected locations within said plasma;

determining a calibrated first dataset curve for each said selected wavelength in said first dataset using said calibration dataset; and determining inaccurate results based upon the variability of the calibrated first dataset curve for a selected wavelength from the plurality of selected wavelengths on location within said plasma.

2. The method of claim 1, whereby said plurality of selected locations within said plasma comprises a plurality of locations along the height of said plasma at a height above the load coil (HALC) between and including 0 and 20 mm.

3. The method of claim 1, whereby said plurality of selected locations within said plasma comprises a plurality of locations along the width of said plasma.

4. The method of claim 1, further comprising the steps of:
diluting said unknown sample;
performing an ICP-AES analysis on said diluted unknown sample using said inductively coupled plasma obtaining a second dataset comprising the light intensity at said one or more selected wavelengths for said plurality of selected locations within said plasma;
determining a calibrated second dataset curve for each said selected wavelength in said second dataset using said calibration dataset;
said step of determining a calibrated second dataset curve accounting for the dilution of said diluted unknown sample;
determining a cross-over point for each said selected wavelength of said calibrated first dataset curve and said calibrated second dataset curve; and
producing a corrected analytical result for each said sought-for analyte at said determined cross-over point.

5. The method of claim 4, whereby said step of diluting said unknown sample comprises diluting said sample by a factor of twenty or less.

6. The method of claim 4, whereby said step of diluting said unknown sample comprises diluting said sample by a factor of ten or less.

7. The method of claim 4, whereby said step of diluting said unknown sample comprises diluting said sample by a factor of two.

8. The method of claim 7, whereby said plurality of locations within said plasma comprises a plurality of locations along the height of said plasma at a height above the load coil (HALC) between and including 0 and 20 mm.

9. The method of claim 4, whereby said plurality of locations within said plasma comprises a plurality of locations along the height of said plasma at a height above the load coil (HALC) between and including 0 and 20 mm.

10. The method of claim 4, whereby
a. said calibrated first dataset curve comprises an apparent concentration for each said one or more sought-for analytes within said unknown sample for each said plurality of selected locations within said plasma; and
b. said calibrated second dataset curve comprises an apparent concentration for each said one or more sought-for analytes within said unknown sample for each said plurality of selected locations within said plasma.

11. The method of claim 4, whereby
a. said calibrated first dataset curve comprises a normalized or relative value for each said plurality of selected locations within said plasma and for each said selected one or more wavelengths; and
b. said calibrated second dataset curve comprises a normalized or relative value for each said plurality of selected locations within said plasma and for each said selected one or more wavelengths.

12. A method for improved inductively coupled plasma-atomic emission spectrometry (ICP-AES) comprising:
performing ICP-AES analysis on one or more known samples using an inductively coupled plasma, obtaining a calibration dataset comprising the light intensity at one or more selected wavelengths for a plurality of selected locations within said plasma;
each said known sample comprising one or more sought-for analytes;
said step of performing ICP-AES analysis on one or more known samples comprising performing ICP-AES analysis on a plurality of concentrations of each said sought-for analyte;
said one or more selected wavelengths emitted by said one or more sought-for analytes;
performing ICP-AES analysis on an unknown sample using said inductively coupled plasma, obtaining a first dataset comprising the light intensity at said one or more selected wavelengths for said plurality of selected locations within said plasma;
diluting said unknown sample;
performing an ICP-AES analysis on said diluted unknown sample using said inductively coupled plasma obtaining a second dataset comprising the light intensity at said one or more selected wavelengths for said plurality of selected locations within said plasma;
determining a calibrated first dataset curve for each said selected wavelength in said first dataset using said calibration dataset whereby said calibrated first dataset curve comprises a concentration of said one or more sought-for analytes within said unknown sample for each said plurality of selected locations within said plasma;
determining a calibrated second dataset curve for each said selected wavelength in said second dataset using said calibration dataset, whereby said calibrated second dataset curve comprises a concentration of said one or more sought-for analytes within said unknown sample for each said selected location within said plasma;
said step of determining a calibrated second dataset curve accounting the dilution of said diluted unknown sample;
determining a cross-over point of said calibrated first dataset curve and said calibrated second dataset curve; and
producing a corrected result at the location within said plasma at said determined cross-over point.

13. The method of claim 12, whereby said step of diluting said sample comprises diluting said sample by a factor of twenty or less.

14. The method of claim 12, whereby said step of diluting said sample comprises diluting said sample by a factor of ten or less.

15. The method of claim 12, whereby said step of diluting said sample comprises diluting said sample by a factor of two.

16. The method of claim 15, whereby said step of performing an ICP-AES analysis on a sample to obtain a first dataset comprises determining a light intensity at height above the load coil (HALC) between and including 0 and 20 mm.

17. The method of claim 12, whereby said step of performing an ICP-AES analysis on a sample to obtain a first dataset comprises determining a light intensity at height above the load coil (HALC) between and including 0 and 20 mm.

18. A method for improved inductively coupled plasma-atomic emission spectrometry (ICP-AES) comprising:
performing ICP-AES analysis on one or more known samples using an inductively coupled plasma, obtaining a calibration dataset comprising the light intensity at one or more selected wavelengths for a plurality of selected locations within said plasma;

each said known sample comprising one or more sought-for analytes;

said one or more selected wavelengths emitted by said one or more sought-for analytes;

said step of performing ICP-AES analysis on one or more known samples comprises performing ICP-AES analysis on a plurality of concentrations of each said sought-for analyte;

performing ICP-AES analysis on an unknown sample using said inductively coupled plasma, obtaining a first dataset comprising the light intensity at said one or more selected wavelengths for said plurality of selected locations within said plasma;

determining a calibrated first dataset curve for each said selected wavelength in said first dataset using said calibration dataset, whereby said calibrated first dataset curve comprises a concentration of said one or more sought-for analytes within said unknown sample for each said selected location within said plasma;

determining inaccurate results based upon the variability of concentration of said one or more sought-for analytes in said calibrated first dataset curve along said plurality of selected locations within said plasma;

diluting said unknown sample by a factor of ten or less;

performing an ICP-AES analysis on said diluted unknown sample using said inductively coupled plasma obtaining a second dataset comprising the light intensity at said one or more selected wavelengths for said plurality of selected locations within said plasma;

determining a calibrated second dataset curve for each said selected wavelength in said second dataset using said calibration dataset, whereby said calibrated second dataset curve comprises a concentration of said one or more sought-for analytes within said unknown sample for each said selected location within said plasma;

said step of determining a calibrated second dataset curve accounting the dilution of said diluted unknown sample;

determining a cross-over point of said calibrated first dataset curve and said calibrated second dataset curve; and producing a corrected concentration for each said sought-for analyte at said determined cross-over point for each said selected wavelength.

19. The method of claim 18, whereby said step of diluting said sample comprises diluting said sample by a factor of two.

20. The method of claim 18, whereby said step of performing an ICP-AES analysis on a sample to obtain a first dataset comprises determining a light intensity at height above the load coil (HALC) between and including 0 and 20 mm.

* * * * *